United States Patent [19]

Lautenschläger et al.

[11] 4,330,550
[45] May 18, 1982

[54] OXOIMIDAZOLINEALKANOIC ACIDS AND THEIR SALTS AND ESTERS, THEIR PREPARATION AND PHARMACEUTICAL COMPOSITIONS CONTAINING THEM

[75] Inventors: Hans-Heiner Lautenschläger, Cologne; Hans Betzing, Kerpen-Horrem; Brigitte Stoll, Cologne, all of Fed. Rep. of Germany

[73] Assignee: A. Nattermann & Cie. GmbH, Cologne, Fed. Rep. of Germany

[21] Appl. No.: 178,450

[22] Filed: Aug. 15, 1980

[30] Foreign Application Priority Data

Aug. 28, 1979 [DE] Fed. Rep. of Germany ....... 2934746

[51] Int. Cl.$^3$ .................. A61K 31/415; C07D 233/30
[52] U.S. Cl. ................................. 424/273 R; 548/320
[58] Field of Search ..................... 548/320; 424/273 R

[56] References Cited

U.S. PATENT DOCUMENTS 4,090,025 5/1978 Raghu et al. ......................... 548/320

Primary Examiner—John M. Ford
Assistant Examiner—Robert C. Whittenbaugh
Attorney, Agent, or Firm—Burns, Doane, Swecker & Mathis

[57] ABSTRACT

ω-(2-Oxo-4-imidazolin-1-yl) alkanoic acids and salts and esters thereof of the formula:

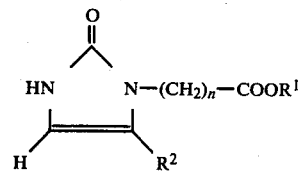

in which n denotes an integer from 1 to 8, $R^1$ denotes H, a non-toxic cation or a straight-chain or branched, saturated hydrocarbon group of 1 to 6 carbon atoms, and $R^2$ denotes an unsubstituted or substituted aromatic radical of formula

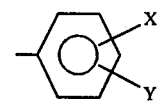

or naphthyl, the substituents X and Y being identical or different and each representing H, halogen or alkoxy have strong antithrombotic activity and an analgesic effect.

24 Claims, No Drawings

OXOIMIDAZOLINEALKANOIC ACIDS AND THEIR SALTS AND ESTERS, THEIR PREPARATION AND PHARMACEUTICAL COMPOSITIONS CONTAINING THEM

DESCRIPTION

The invention relates to imidazoline derivatives having pharmaceutical utility, their preparation, and their use.

More particularly, the present invention provides the ω-(2-oxo-4-imidazolin-1-yl)-alkanoic acids and salts and esters thereof of the formula:

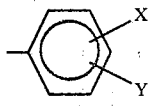     I in which n denotes an integer from 1 to 8, $R^1$ denotes H, a non-toxic cation or a straight-chain or branched, saturated hydrocarbon group of 1 to 6 carbon atoms, and $R^2$ denotes an unsubstituted or substituted aromatic radical of formula

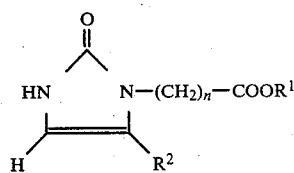

or naphthyl, the substituents X and Y being identical or different and each representing H, halogen or alkoxy. These compounds have a strong antithrombotic activity, are suitable as antiarteriosclerotic medicaments, and also display analgesic effects.

The invention also provides a process for the preparation of the ω-(2-oxo-4-imidazolin-1-yl)-alkanoic acids of the general formula (I), which comprises reacting a compound of the formula:

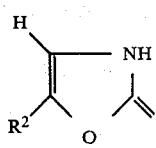     II wherein $R^2$ is as defined above, in an aprotic organic solvent, such as, for example, dimethylformamide, acetone or benzene, if appropriate with the addition of a basic catalyst, such as triethylamine, pyridine, an alkali metal carbonate or an alkali metal cyanate, with ω-alkoxycarbonylalkyl isocyanate of the formula:

     III wherein n is as defined above and R is a methyl or ethyl group, to give an intermediate N-(ω-alkoxycarbonylalkyl)-2-oxo-4-oxazoline-3-carboxamide of the formula:

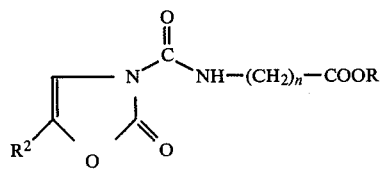     IV wherein n, R and $R^2$ are as defined above, after which this intermediate is treated with acid to give a compound of formula I in which $R^1$ is hydrogen.

The compounds of the formula IV are converted in an acid medium, such as, for example, glacial acetic acid/HCl or glacial acetic acid/HBr, with hydrolysis and scission of carbon dioxide, into compounds of the formula:

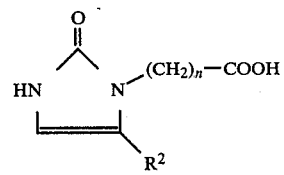     Ia

The compounds of the general formula (Ia), which are compounds of the formula (I) when $R^1$ is hydrogen, can be converted into their non-toxic salts, especially their alkali metal salts, in accordance with known procedures by reaction with, for example, an alkali metal hydroxide or alkali metal carbonate, or into their esters by treatment with an alcohol of the formula $R^1OH$ (in which $R^1$ is a straight-chain or branched saturated hydrocarbon group of 1 to 6 carbon atoms in the presence of an acid catalyst.

The preparation of the imidazolinones of the formula (I) may be represented by the following equation:

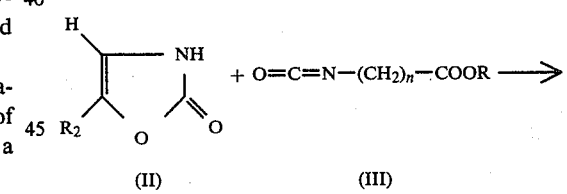

(II)    (III)

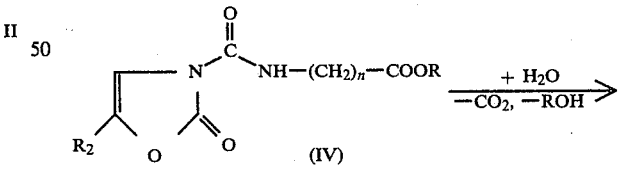

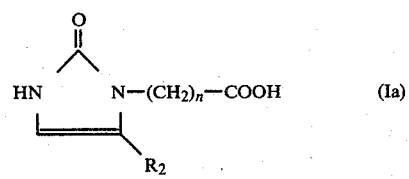     (Ia)

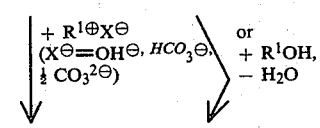

-continued

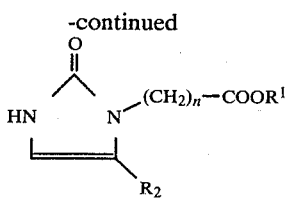

The imidazolinones of formula (I) can also be prepared by reacting salts of amino-ketones of formula:

wherein $R^2$ is as defined above and X is $Cl^\ominus$, $Br^\ominus$ or $HSO_4^\ominus$, with ω-alkoxycarbonylalkyl isocyanates of formula (III) in an aprotic organic solvent, such as, for example, benzene, acetone or dimethylformamide, at a temperature between 0° and 100° C., with the addition of an organic base, such as, for example, triethylamine or pyridine, the reaction being finally completed by acidifying and heating the reaction mixture.

The imidazolinones of formula (I) display valuable pharmacological properties, and in particular antithrombotic, antiarteriosclerotic and analgesic activity. They are excellently tolerated by the stomach and can, therefore, be used particularly for the treatment of thrombotic and arteriosclerotic diseases, while having at the same time advantageous gastro-intestinal properties.

Hitherto, anticoagulants have been employed in the prophylaxis of thrombosis. At sufficiently high dosage, anticoagulants prevent the formation of fibrin and thus the formation of a red thrombus, but they cannot affect the initial aggregation of the thrombocytes, that is to say the formation of the platelet-thrombus.

Now that the significance of the thrombocytes in thrombogenesis has become known, substances which inhibit such aggregation, such as, for example, acetylsalicyclic acid, have become increasingly more important as antithrombotics. However, acetylsalicyclic acid has a number of undesirable side-effects. There is therefore a need for new inhibitors of the aggregation of thrombocytes, which display a good antithrombotic action and are considerably better tolerated by the stomach than acetylsalicyclic acid.

The compounds of formula I have a strong inhibiting effect on the aggregation of thrombocytes as well as an adhesion-inhibiting effect, combined with a low toxicity:

| $LD_{50}$ in mice/intravenous | 922 mg/kg (7 days) |
| $LD_{50}$ in mice/administered orally | 2,002 mg/kg (7 days) | and are very well tolerated by the stomach.

The compounds of formula I can advantageously be combined with other active compounds, such as, for example, anticoagulants, in particular heparin, heparinates and coumarin derivatives. It is desirable, particularly in the prophylaxis of thromboembolic complications, to exert an influence on the inhibition of the aggregation of thrombocytes and on the inhibition of coagulation of the blood. Here too, the compounds of the invention have an excellent activity in combination with anticoagulants, especially with heparin and heparinates, as shown by the following investigations.

The aggregation of platelets in the presence of the compounds of the invention has been tested by the collagen-induced aggregation method of Born., Nature 4832/927, 29 (1962). The effect of the compounds in inhibiting thrombocyte aggregation was investigated in vitro on human plasma with a high platelet content. The results are shown in the Table which follows.

The percentage inhibition of collagen-induced aggregation in vitro by compounds from the Examples indicated in Table 3, or combinations thereof with heparin, at a final concentration of 0.3 or 0.6 μmol of compound per ml of human plasma with a high platelet content, can be seen from the following Table.

| Compounds from the Examples of Table 3 | % inhibition compared with the control |
|---|---|
| 1 c | 80% (0.3 μmol 1c/ml) |
| 2 c | 46% (0.3 μmol 2c/ml) |
| 5 c | 63% (0.3 μmol 5c/ml) |
| Combination 1c + sodium heparinate | 85% (0.3 μmol 1c/ml; Heparin 200 IU/ml) |
| 1c + sodium heparinate | 82% (0.6 μmol 1c/ml; Heparin 200 IU/ml) |

The compounds of formula (I) can be administered, for example, orally, by injection or rectally in suitable pharmaceutical compositions, which can be solid or liquid in the form of suspensions or solutions, comprising a compound of formula I together with a pharmaceutically suitable diluent or excipient. Examples of formulations of this type are tablets, powders, capsules, granules, pastilles, ampoules, syrups and suppositories.

The abovementioned compositions can additionally contain further active compounds, in particular anticoagulants, for example heparin, heparin salts and coumarin derivatives.

The effective quantity of the compounds of the formula (I) can be altered freely, in accordance with the dosage desired, but is usually about 0.1 to 80%, relative to the combined quantity of excipient or diluent and the compound of the formula (I). Quite generally, it is possible to use any desired concentration for the required administration in dosages in the range from 0.1 to 100 mg/kg of body weight per day.

Excipients or diluents can be pharmaceutically tolerated liquids or solids, and, as used herein, the term excipient also includes adjuvants. Examples of liquid excipients are distilled water for injection, isotonic sodium chloride solution, Ringer's solution, Locke's solution, ethylene glycol, polyethylene glycol, ethyl alcohol, propylene glycol, glycerol and vegetable oils. Solid excipients include, for example, sodium chloride, glucose, lactose, starch, sucrose, cetyl alcohol, cocoa butter and magnesium stearate.

The preparation of the compounds according to the invention is illustrated in greater detail by means of the following Examples:

EXAMPLE 1

(a) Preparation of N-(ethoxycarbonylheptyl)-2-oxo-5-phenyl-4-oxazolin-3-ylcarboxamide.

16.1 g (0.1 mol) of 5-phenyl-4-oxazolin-2-one are dissolved in 100 ml of absolute DMF and 25.6 g (0.12 mol) of ethoxycarbonylheptyl isocyanate are added. The mixture is stirred for 24 hours at 50°–60° C., water is added and the oily/crystalline precipitate which is formed is separated, washed with water and dried in vacuo at room temperature. The crude product is recrystallised from ethanol.

Yield: 27 g (72%), melting point 97°–99° C.

The Examples 2a–10a, contained in Table 1, were carried out analogously, some carboxamides being processed further in the form of crude products, as indicated.

(b) Preparation of 8-(2-oxo-5-phenyl-4-imidazolin-1-yl)-caprylic acid.

A mixture of 800 ml of glacial acetic acid and 80 ml of 63 percent hydrobromic acid is poured over 37.4 g (0.1 mole) of N-ethyoxycarbonylheptyl-2-oxo-5-phenyl-4-oxazolin-3-ylcarboxamide and the mixture is heated under reflux for 2 hours and evaporated as completely as possible in vacuo. The residue is stirred with water. The crude product which is precipitated is separated and washed with a little water. After drying, the compound is purified by column chromatography (silica gel//CHCl₃/methanol).

Yield: 18.1 g (60%), melting point 83°–85° C.

The Examples 2b–10b, contained in Table 2, were carried out analogously.

(c) Preparation of the sodium salt of 8-(2-oxo-5-phenyl-4-imidazolin-1-yl)-caprylic acid.

25 percent alcohol is added to a mixture of 30.2 g (0.1 mol) of 8-(2-oxo-5-phenyl-4-imidazolin-1-yl)-caprylic acid and 8.4 g (0.1 mol) of anhydrous sodium bicarbonate and the mixture is stirred, while being heated gently, until dissolution is complete. The solution is concentrated to dryness in vacuo and the solid residue is powdered.

Yield: 32.4 g (100%).

The Examples 2c–10c, contained in Table 3, were carried out analogously.

In the following Tables, the melting points quoted were determined with an electrothermal apparatus for determining melting points and are not corrected. The IR spectra were recorded with the Perkin-Elmer 257 apparatus, the NMR spectra with the Bruker 60 MHz and 80 MHz apparatuses (internal standard: tetramethylsilane, except for D₂O recordings: the sodium salt of 3-trimethylsilylpropionic acid) and the mass spectra with the Varian MAT-331A (70 eV) apparatus.

The following abbreviations apply to the ¹H-NMR data quoted:

Sol: solvent
DMF: dimethylformamide
DMSO: dimethyl sulphoxide
s: singlet
d: doublet
t: triplet
q: quartet
m: multiplet
mc: multiplet centered on

TABLE 1

N-(ω-Alkoxycarbonylalkyl)-2-oxo-4-oxazoline-3-carboxamides (IV) obtained by reacting 4-oxazolin-2-ones (II) with ω-alkoxycarbonylalkyl isocyanates (III)

$$\text{structure IV: } R^2\text{-substituted 4-oxazolin-2-one with } -C(O)-NH-(CH_2)_n-COOR$$

| Ex. No. | n | R | R² | Melting point in [°C] | IR data in [cm⁻¹] |
|---|---|---|---|---|---|
| 1a | 7 | C₂H₅ |  | 97–99 | in KBr: 3340, 3140, 1765, 1734, 1700, 1545 |
| 2a | 6 | C₂H₅ |  | 92–95 | in KBr: 3340, 3140, 1760, 1735, 1712, 1550 |
| 3a | 1 | C₂H₅ |  | 180–182 | in KBr: 3320, 3140, 1772, 1740, 1715, 1530 |
| 4a | 1 | C₂H₅ | 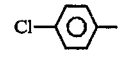 | 211–215 | in KBr: 3330, 3140, 1780, 1740, 1710, 1530 |
| 5a | 6 | C₂H₅ | 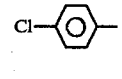 | 119–121 | in KBr: 3340, 3140, 1762, 1735, 1708, 1540 |
| 6a | 5 | C₂H₅ |  | not determined | in CCl₄: 3350, 3170, 1775, 1735, 1725, (shoulder), 1535 |
| 7a | 8 | C₂H₅ |  | not determined | in KBr: 3340, 3140, 1755, 1735, 1705, 1540 |
| 8a | 6 | C₂H₅ | 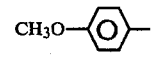 | not determined | Film: 3350, 3150, 1760, 1735, 1705, 1540 |
| 9a | 6 | C₂H₅ | 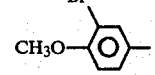 | not determined | in KBr: 3350, 3150, 1755, 1735, 1710, 1540 |
| 10a | 7 | CH₃ | 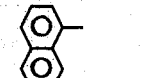 | not determined | Film: 3330, 3150, 1765, 1730, 1765, 1730, 1705, 1535 |

TABLE 2

Preparation of ω-(2-oxo-4-imidazolin-1-yl)-alkanoic acids (I) from N-(ω-alkoxycarbonylalkyl)-2-oxo-4-oxazoline-3-carboxamides (IV)

| Ex. No. | n | R² | Melting point in [°C.] | IR frequencies of the carbonyl groups in [cm⁻¹] | MS data in [m/e] |
|---|---|---|---|---|---|
| 1b | 7 |  | 83–85 | 1725, 1660 (KBr) | 302 (M⁺, 55%), 285 (M⁺—OH, 38%), 243 (M⁺—CH₂COOH, 15%), 173 (37%), 160 (100%), 145 (9%) |
| 2b | 6 |  | 132–137 | 1720, 1655 (KBr) | 288 (M⁺(M⁺—OH, 38%), 229 (M⁺—CH₂COOH, 20%), 173 (39%), 160 (100%), 145 (10%) |
| 3b | 1 |  | 255–258 | 1722, 1620 (KBr) | 218 (M⁺, 100%), 174 (M⁺—CO₂, 23%), 173 (M⁺—COOH, 67%), 160 (1%), 145 (24%) |
| 4b | 1 |  | 272–275 | 1728, 1645 (KBr) | 252 (M⁺, 100%), 208 (M⁺—CO₂, 31%), 207 (M⁺—COOH, 71%), 194 (3%), 179 (30%) |
| 5b | 6 |  | 156–160 | 1710, 1660 (KBr) | 322 (M⁺, 81%), 305 (M⁺—OH, 32%), 263 (M⁺—CH₂COOH, 18%), 207 (31%), 194 (100%), 179 (11%) |
| 6b | 5 |  | 143–145 | 1725, 1660 (KBr) | 274 (M⁺, 100%), 257 (M⁺—OH, 42%), 215 (M⁺—CH₂COOH, 25%), 173 (42%), 160 (96%), 145 (11%) |
| 7b | 8 |  | 103–107 | 1725, 1660 (KBr) | 316 (M⁺, 76%), 299 (M⁺—OH, 35%), 257 (M⁺—CH₂COOH, 11%), 173 (38%), 160 (100%), 145 (10%) |
| 8b | 6 |  | 170–172 | 1715, 1660 (KBr) | 318 (M⁺, 100%), 301 (M⁺—OH, 29%), 259 (M⁺—CH₂COOH, 11%), 203 (41%), 190 (83%), 175 (35%) |
| 9b | 6 |  | 187–189 | 1715, 1660 (KBr) | 396 (M⁺, 100%), 379 (M⁺—OH, 28%), 337 (M⁺—CH₂COOH, 14%), 281 (23%), 268 (66%), 253 (34%) |
| 10b | 7 | 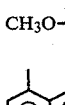 | Oil | 1700, 1660 (Film) | 352 (M⁺, 100%), 335 (M⁺—OH, 36%), 293 (M⁺—CH₂COOH, 13%), 223 (46%), 210 (68%), 195 (3%) |

TABLE 3

Preparation of the sodium salts of formula (I) (R¹ = Na) from the ω-(2-oxo-4-imidazolin-1-yl)-alkanoic acids (I) (R¹ = H)

| Ex. No. | n | R² | ¹H—NMR data of the sodium salts I (R¹ = Na, solvent: D₂O) or - if I (R¹ = Na) was not determined - the data of the free acids I (R¹ = H, the solvent being indicated). δ-values in [ppm]. | IR frequencies of the carbonyl groups in [cm⁻¹] |
|---|---|---|---|---|
| 1c | 7 |  | 0.8–1.8(m,10H[CH₂]),2.16(t,J = 7Hz, 2 H[CH₂]), 3.57 (mc, broad, 2 H[CH₂]), 6.33 (s,1H, [heterocyclic-CH]), 7.20 (s, 5H [aromatic]). | 1675, 1565 (KBr) |
| 2c | 6 |  | Free acid (see Example 2b), Sol.: DMF—d₇: 0.4–1.33 (m, 8H[CH₂]), 1.70 (t,J = 7Hz, 2 H [CH₂]), 3.27 (t, J = 6Hz,2H[CH₂]), 6.13 (s,1H[heterocyclic-CH]), 6.97 (s,5H[aromatic]), 9.87 (s,broad, 1H, exchangeable with D₂O) | 1675, 1560 (KBr) |
| 3c | 1 |  | Free acid (see Example 3b), Sol: DMSO—d₆: 4.40 (s,2H[CH₂]), 6.60 (s,1H[heterocyclic-CH]), 7.43 (s, 5H [aromatic]), 10.10 (s,broad, 1H, exchangeable with D₂O). | 1720, 1615 (KBr) |
| 4c | 1 |  | 4.19 (s,2H[CH₂]), 6.57 (s,1H[heterocyclic-CH]), 7.37 (mc,4H[aromatic]). | 1710, 1605 (KBr) |

TABLE 3-continued

Preparation of the sodium salts of formula (I) ($R^1$ = Na) from the ω-(2-oxo-4-imidazolin-1-yl)-alkanoic acids (I) ($R^1$ = H)

| Ex. No. | n | $R^2$ | $^1$H—NMR data of the sodium salts I ($R^1$ = Na, solvent: $D_2O$) or - if I ($R^1$ = Na) was not determined - the data of the free acids I ($R^1$ = H, the solvent being indicated). δ-values in [ppm]. | IR frequencies of the carbonyl groups in [cm$^{-1}$] |
|---|---|---|---|---|
| 5c | 6 | Cl—⬡— | Free acid (see Example 5b), Sol.: DMF—d$_7$: 1.27 (mc, 8H[CH$_2$]),2.22 (t, J = 7Hz, 2H[CH$_2$]), 3.73 (t, J = 7Hz,2H[CH$_2$]), 6.67 (s,1H [heterocyclic-CH]), 7.50 (mc,4H[aromatic]), 10.30(s, broad, 1H, exchangeable with D$_2$O). | 1680, 1560 (KBr) |
| 6c | 5 | ⬡— | 1.30 (mc,6H[CH$_2$]), 2.04 (t,J = 7Hz, 2H[CH$_2$]), 3.61 (t, J = 6Hz, 2H[CH$_2$]), 6.36 (s, 1H[heterocyclic-CH]), 7.35 (s, 5H[aromatic]). | 1680, 1580 (KBr) |
| 7c | 8 | ⬡— | 0.66-1.69 (m,12H[CH$_2$]), 2.11 (t, J = 7Hz, 2H [CH$_2$]), 3.64 (mc,broad,2H [CH$_2$]), 6.33 (s, 1H[heterocyclic-CH]) 7.21 (s, 5H[aromatic]). | 1675, 1560 (KBr) |
| 8c | 6 | CH$_3$O—⬡— | Free acid (see Example 8b), Sol.: DMSO—d$_6$: 1.22 (mc, 8H[CH$_2$]), 2.14 (t, J = 7Hz, 2H [CH$_2$]), 3.38 (mc, broad, 2H[CH$_2$]), 3.75 (s,3H [CH$_3$]), 5.09 (s,1H[heterocyclic-CH]), 6.88-7.22 (m,4H[aromatic]), 10.90 (s,broad,1H,exchangeable with D$_2$O). | 1675, 1560 (KBr) |
| 9c | 6 | CH$_3$O—⬡—Br | Free acid (see Example 9b), Sol.: DMSO—d$_6$: 1.20 (mc,8H[CH$_2$]), 2.13 (t, J = 6Hz, 2H[CH$_2$]), 3.63 (t,broad,2H[CH$_2$]), 3.90 (s,3H[CH$_3$]), 6.50 (s,1H [heterocyclic-CH]), 7.0-7.7 (m,3H [aromatic]), 10.23 (s,broad,1H, exchangeable with D$_2$O). | 1675, 1560 (KBr) |
| 10c | 7 | (naphthyl) | 0.3-1.5 (m,10H[CH$_2$]),2.00(t, J = 7.5 Hz, 2H[CH$_2$]), 3.22 (mc,broad 2H[CH$_2$]), 6.08 (s,1H[heterocyclic-CH]), 6.83-7.61 (m,7H[aromatic]). | 1675, 1517 (KBr) |

EXAMPLE 11

Preparation of the methyl ester of 8-(2-oxo-5-phenyl-4-imidazolin-1-yl)-caprylic acid.

10 ml of methanol are added to 15.1 g (0.05 mol) of 8-(2-oxo-5-phenyl-4-imidazolin-1-yl)-caprylic acid and hydrogen chloride is passed into the mixture to saturation point. The mixture is heated under reflux for 2 hours, while HCl is still passed in, and is then concentrated in vacuo. The residue is taken up in chloroform. The chloroform solution is extracted several times with Na$_2$CO$_3$ solution and then washed with water and dried over Na$_2$SO$_4$. The solvent is removed and the oily residue is dried in vacuo.

Yield: 15.3 g (97%), colourless oil.

The Examples 12-14, contained in Table 4, were carried out analogously, the reaction mixture in Example 14 not being heated under reflux, but at approximately 100° C. and the oily residue being additionally purified by column chromatography (silica gel/CHCl$_3$/methanol).

TABLE 4

Preparation of the alkyl esters of formula (I) ($R^1$ = alkyl) from the ω-(2-oxo-4-imidazolin-1-yl)-alkanoic acids (Ia)

| Ex. No. | n | $R^1$ | $R^2$ | IR frequencies of the carbonyl groups in [cm$^{-1}$] | MS data in [m/e] |
|---|---|---|---|---|---|
| 11 | 7 | CH$_3$ | ⬡— | 1735, 1680 Film | 316 (M$^+$, 96%), 299 (M$^+$—OH, 56%), 285 (M$^+$—CH$_3$O, 18%), 160 (100%) |

TABLE 4-continued

Preparation of the alkyl esters of formula (I) ($R^1$ = alkyl) from the ω-(2-oxo-4-imidazolin-1-yl)-alkanoic acids (Ia)

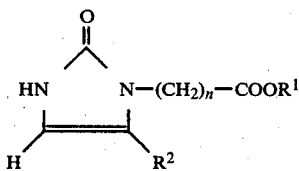

| Ex. No. | n | $R^1$ | $R^2$ | IR frequencies of the carbonyl groups in [cm$^{-1}$] | MS data in [m/e] |
|---|---|---|---|---|---|
| 12 | 7 | C$_2$H$_5$ | —C$_6$H$_5$ | 1730, 1680 Film | 330 (M$^+$, 93%), 313 (M$^+$—OH, 53%), 285 (M$^+$—C$_2$H$_5$O, 30%), 160 (100%) |
| 13 | 7 | CH(CH$_3$)$_2$ | —C$_6$H$_5$ | 1730, 1680 Film | 344 (M$^+$, 96%), 327 (M$^+$—OH, 27%), 302 (M$^+$—C$_3$H$_6$, 29%), 285 (M$^+$—C$_3$H$_7$O 70%), 160 (100%) |
| 14 | 7 | n-C$_6$H$_{13}$ | —C$_6$H$_5$ | 1730, 1680 Film | 386 (M$^+$, 100%), 369 (M$^+$—OH, 40%), 285 (M$^+$—C$_6$H$_{13}$O, 29%), 160 (57%) |

The following Examples describe pharmaceutical compositions comprising compounds of formula I and pharmaceutically conventional excipients or auxiliaries, which can be used as medicaments:

EXAMPLE 15: TABLETS

A mixture consisting of 50 g of the sodium salt of 8-(2-oxo-5-phenyl-4-imidazolin-1-yl)-caprylic acid, 50 g of lactose, 16 g of maize starch, 2 g of cellulose powder and 2 g of magnesium stearate is compressed in the customary manner to give tablets in such a way that each tablet contains 250 mg of the active compound.

EXAMPLE 16: DRAGÉES

Tablets are compressed as in Example 15 and are then coated in the customary manner with a coating consisting of sugar, maize starch, talc and tragacanth.

EXAMPLE 17: AMPOULES 100 g of sodium salt of 8-(2-oxo-5-phenyl-4-imidazolin-1-yl)-caprylic acid are dissolved in a mixture of 9.5 l of twice distilled water and 0.5 l of ethylene glycol. The mixture is filtered under sterile conditions and 10 ml portions of the resulting solution are filled under sterile conditions into ampoules, which are then sealed by fusion.

Tablets, dragées and ampoules containing one or more active compounds of the formula I with or without the addition of an anticoagulant can be obtained analogously, as shown in the following Examples.

EXAMPLE 18

5 ml of an injection solution contain 20,000 IU (approximately 122–162 IU/mg) of sodium heparinate and 1 g of the sodium salt of 8-(2-oxo-5-phenyl-4-imidazolin-1-yl)-caprylic acid.

EXAMPLE 19

5 ml of an injection solution contain 10,000 IU (approximately 122–162 IU/mg) of sodium heparinate and 2 g of the sodium salt of 8-(2-oxo-5-phenyl-4-imidazolin-1-yl)-caprylic acid.

We claim:

1. ω-(2-Oxo-4-imidazolin-1-yl)-alkanoic acids, salts and ester thereof of the formula

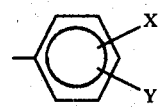

in which n denotes an integer from 1 to 8, $R^1$ denotes H, a non-toxic cation, or a straight-chain or branched saturated hydrocarbon group of 1 to 6 carbon atoms, and $R^2$ is selected from the group consisting of naphthyl, or an unsubstituted or substituted aromatic radical of formula wherein the substituents X and Y, which may be the same or different, represent H, halogen or alkoxy.

2. 8-(2-Oxo-5-phenyl-4-imidazolin-1-yl)-caprylic acid and pharmaceutically tolerated salts and esters thereof.

3. 7-(2-Oxo-5-phenyl-4-imidazolin-1-yl)-heptanoic acid and pharmaceutically tolerated salts and esters thereof.

4. (2-Oxo-5-phenyl-4-imidazolin-1-yl)-acetic acid and pharmaceutically tolerated salts and esters thereof.

5. 5-(4-Chlorophenyl)-2-oxo-4-imidazolin-1-yl-acetic acid and pharmaceutically tolerated salts and esters thereof.

6. 7-[5-(4-Chlorophenyl)-2-oxo-4-imidazolin-1-yl]-heptanoic acid and pharmaceutically tolerated salts and esters thereof.

7. 6-(2-Oxo-5-phenyl-4-imidazolin-1-yl)-caproic acid and pharmaceutically tolerated salts and esters thereof.

8. 9-(2-Oxo-5-phenyl-4-imidazolin-1-yl)-pelargonic acid and pharmaceutically tolerated salts and esters thereof.

9. 7-[5-(4-Methoxyphenyl)-2-oxo-4-imidazolin-1-yl]-heptanoic acid and pharmaceutically tolerated salts and esters thereof.

10. 7-[5-(3-Bromo-4-methoxyphenyl)-2-oxo-4-imidazolin-1-yl]-heptanoic acid and pharmaceutically tolerated salts and esters thereof.

11. 8-[5-(1-Naphthyl)-2-oxo-4-imidazolin-1-yl]-caprylic acid and pharmaceutically tolerated salts and esters thereof.

12. A process for the preparation of an ω-(2-oxo-4-imidazolin-1-yl)-alkanoic acid represented by the structural formula

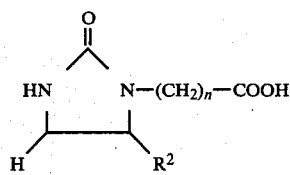

in which n denotes an integer from 1 to 8, and $R^2$ is selected from the group consisting of naphthyl, or aromatic radical of formula

wherein the substituents X and Y, which may be the same or different, represent H, halogen or alkoxy; which comprises reacting a compound of the formula:

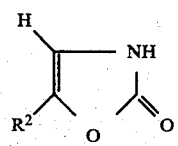

in which $R^2$ is as defined above, in an aprotic organic solvent, with an ω-alkoxycarbonylalkyl isocyanate of the formula:

wherein n is as defined above and R is methyl or ethyl, to give the intermediate of the formula:

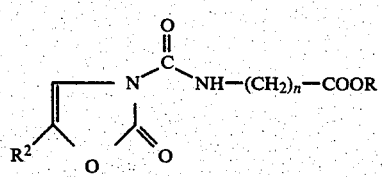

in which R, $R^2$ and n are as defined above; and contacting said intermediate with an acid in a manner sufficient to yield the compound of formula I.

13. The process according to claim 12, in which the compound of formula IV is converted into the acid of formula I by treatment with glacial acetic acid and HBr.

14. The process according to claims 12, in which the reaction of the compounds of formulae II and III is carried out in the presence of a basic catalyst.

15. The process according to claim 12 which comprises dissolving a compound of structural formula II in dimethylformamide; adding a compound of formula III to said solution and stirring the resulting mixture for about 24 hours at a temperature between about 50° and 60° C. to form the intermediate carboxamide compound of formula IV; precipitating said carboxamide with water; recovering and drying said precipitate in vacuo at room temperature; recrystallizing the crude product from ethanol; contacting said product with a mixture of glacial acetic acid and hydrobromic acid and heating the resulting mixture for about 2 hours; evaporating the volatiles of said mixture in vacuo to yield a residue; stirring the residue with water to precipitate a compound as represented by formula I; washing said precipitate with water and recovering the same.

16. The process of claim 12 which further comprises reacting the free acid of formula I derived from claim 12 with a non-toxic base or carbonate salt in a solvent.

17. The process according to claim 16 in which the said salt is an alkali metal salt.

18. The process of claim 12 which further comprises mixing the acid of formula I with alcohol and anhydrous sodium bicarbonate; stirring the resulting mixture at a temperature sufficient to dissolve the bicarbonate and acid; concentrating the solution to dryness in vacuo and recovering the corresponding salt of the acid.

19. The process of claim 12 which further comprises reacting the free acid of formula I in the presence of an acid catalyst, with an alcohol of the formula $R^1OH$ in which $R^1$ is a straight-chain or branched saturated hydrocarbon group of 1 to 6 carbon atoms to yield the ester of said acid.

20. The process according to claim 19 which comprises mixing the acid of formula I with methanol; passing hydrogen chloride into the mixture; when the hydrogen chloride has reached the saturation point in said mixture heating the mixture under reflux for 2 hours while continuing to pass hydrogen chloride therethrough; concentrating the mixture in vacuo and dissolving the corresponding methyl ester of the acid in chloroform; extracting said ester containing chloroform solution with $Na_2CO_3$; and washing the extracted product with water.

21. An antithrombotic pharmaceutical composition comprising an antithrombotically effective amount of a compound as claimed in any one of claims 1 to 11 together with a pharmaceutically suitable diluent or excipient.

22. A composition according to claim 21, which additionally contains an anticoagulant.

23. A composition according to claim 22 in which the anticoagulant is heparin, a heparin salt or a coumarin derivative.

24. A composition according to claim 21, wherein the pharmaceutically suitable diluent or excipient are selected to provide tablets, dragees, ampoules or injectable solutions.

* * * * *